United States Patent [19]

Arakawa et al.

[11] Patent Number: 4,504,692

[45] Date of Patent: Mar. 12, 1985

[54] PROCESS FOR PRODUCING 1,3-BUTADIENE

[75] Inventors: Masatoshi Arakawa; Hayao Yoshioka; Kazuyoshi Nakazawa, all of Tokyo, Japan

[73] Assignee: Japan Synthetic Rubber Co., Ltd., Tokyo, Japan

[21] Appl. No.: 588,085

[22] Filed: Mar. 9, 1984

[30] Foreign Application Priority Data

Mar. 14, 1983 [JP] Japan ............................ 57-40572

[51] Int. Cl.$^3$ ........................ C07C 5/09; C07C 5/333
[52] U.S. Cl. .............................. 585/633; 585/616; 585/617
[58] Field of Search ..................... 585/616, 617, 633

[56] References Cited

U.S. PATENT DOCUMENTS

| 2,322,122 | 6/1943 | Frolich et al. | 585/616 |
|---|---|---|---|
| 2,370,513 | 2/1945 | Amos et al. | 585/617 |
| 2,376,061 | 5/1945 | Jones | 585/616 |
| 2,382,473 | 8/1945 | Frey | 585/616 |
| 2,415,921 | 2/1947 | Wagner | 585/633 |
| 2,437,773 | 3/1948 | Whaley | 585/617 |
| 2,554,054 | 5/1951 | Owen | 585/633 |
| 3,232,849 | 2/1966 | Renberg | 585/633 |
| 3,907,919 | 9/1975 | Lo et al. | 585/617 |

FOREIGN PATENT DOCUMENTS

| 26206 | 3/1974 | Japan | 585/616 |
|---|---|---|---|
| 0857093 | 8/1981 | U.S.S.R. | 585/616 |
| 0857094 | 8/1981 | U.S.S.R. | 585/616 |

OTHER PUBLICATIONS

Encyclopedia of Chem. Proc. and Design, vol. 5, pp. 144–154.
Chemical Engineering 39, pp. 146–148.

*Primary Examiner*—Delbert E. Gantz
*Assistant Examiner*—Helane Maull Myers
*Attorney, Agent, or Firm*—Oblon, Fisher, Spivak, McClelland & Maier

[57] ABSTRACT

A process for producing 1,3-butadiene which comprises feeding a fraction comprising $C_4$-paraffins and $C_4$-olefins as the main components and being free from isobutene, 1,3-butadiene and $C_4$-acetylenes to a dehydrogenation or oxidative dehydrogenation step (step A), where the n-butenes contained therein is converted to 1,3-butadiene; feeding the 1,3-butadiene-containing hydrocarbon fraction thus obtained (fraction C) to an extractive distillation column (column B), in which said fraction C is distilled in an atmosphere of a selective solvent while obtaining a fraction comprising $C_4$-paraffins as the main hydrocarbon component from the top of the column; withdrawing a fraction comprising n-butenes as the main component as a side stream from a stage on the upper side of the aforementioned fraction C-feeding stage and on the lower side of the selective solvent-feeding stage and recycling it into step A while withdrawing a fraction comprising 1,3-butadiene as the main hydrocarbon component and also containing the selective solvent from the bottom of column B; and separating 1,3-butadiene from the 1,3-butadiene-containing fraction.

4 Claims, 4 Drawing Figures

PROCESS FOR PRODUCING 1,3-BUTADIENE

BACKGROUND OF THE INVENTION

1. Field of the Invention

The present invention relates to a process for producing 1,3-butadiene (hereinafter, simply referred to as "butadiene"), and more particularly to a process for producing butadiene from a $C_4$-hydrocarbon fraction.

2. Description of Prior Art

The production of butadiene by the dehydrogenation or oxidative dehydrogenation of 1-butene and/or 2-butene (hereinafter, sometimes referred to as "n-butuenes") in the presence of a selective catalyst is well-known, and is practised on an industrial scale. The n-butenes used as the starting material in this process are obtained by, for example, the dehydrogenation of n-butane, and also formed as by-products in the fluidized catalytic cracking (FCC) of heavy oil or the steam cracking of naphtha, kerosene, light oil or the like.

Amongst these $C_4$-fractions, by-products in the steam-cracking of naphtha or the like contain a large quantity (for example, 25–50% by weight) of butadiene. Therefore, the butadiene is first separated from the by-products by extraction, the residual fraction (spent $C_4$ fraction) is used as a source for n-butenes.

The $C_4$-fraction obtained as a by-product in the FCC and the spent $C_4$-fraction obtained in the steam-cracking are mixtures comprising i-butane, i-butene, n-butane and the like in addition to n-butenes. It is preferred that the starting material used in the production of butadiene by dehydrogenation or oxidative dehydrogenation satisfies the requirements that the n-butenes concentration in $C_4$-fraction is high and substantially no i-butene is contained. For example, UOP, 1978, Technology Conference-H-11 describes that the n-butenes concentration in the starting material for the production of butadiene may be about 90% or more but the i-butene concentration in the starting material must be about 0.3% or less.

Separation of a specific component from a $C_4$-fraction by the conventional distillation is practically impossible, because the boiling points of components contained in the $C_4$-fraction are so close to one another as shown in Table 1, and a variety of methods for the separation have hitherto been studied and developed.

TABLE 1

| Main $C_4$ hydrocarbons | Boiling points (°C.) |
| --- | --- |
| i-Butane | −11.7 |
| i-Butene | −6.9 |
| 1-Butene | −6.3 |
| 1,3-Butadiene | −4.4 |
| n-Butane | −0.5 |
| t-2-Butene | 0.9 |
| c-2-Butene | 3.7 |

Table 2 shows conceptionally how $C_4$-paraffins and $C_4$-olefins are separated by main methods for separating $C_4$-hydrocarbons.

TABLE 2

| Component | Separation method | | | | | | | |
| --- | --- | --- | --- | --- | --- | --- | --- | --- |
| | A | B | C | D | E | F | G | H |
| i-Butane | x | x | ◉ | ◉ | x | x | ◉ | ◉ |
| n-Butane | o | x | ◉ | ◉ | o | x | ◉ | ◉ |
| i-Butene | x | ◉ | x | x | x | ◉ | ◉ | x |
| 1-Butene | x | ◉ | ◉ | ◉ | ◉ | ◉ | x | ◉ |
| t-2-Butene | ◉ | ◉ | ◉ | ◉ | ◉ | ◉ | ◉ | ◉ |
| c-2-Butene | ◉ | ◉ | ◉ | ◉ | ◉ | ◉ | ◉ | ◉ |

Note:
(1) Separation methods
A: Distillation
B: Extractive distillation
C: Absorption by sulfuric acid (separation of i-butene by absorbing it in 50–65% by weight sulfuric acid)
D: Etherification (separation of i-butene by converting it to methyl t-butyl ether or the like)
E: Vapor phase adsorption (Olefin SIV (registered trade mark) method - UCC)
F: Liquid phase adsorption ($C_4$ OLEX (registered trade mark) method - UOP)
G: Liquid phase adsorption (SORBUTENE (registered trade mark) method - UOP)
H: Dimerizing distillation (separation of i-butene by dimerizing it)
(2) Degree of separation from 2-butene
◉: Mostly entrained
o: Considerably entrained
x: Mostly separated As is apparent from Table 2, there is no single method by which the n-butenes for use as a starting material for the production of butadiene by dehydrogenation or oxidative dehydrogenation, which n-butenes contain substantially no i-butene and have been substantially freed from $C_4$-paraffins, can be separated from the above-mentioned various, industrially available $C_4$-fractions in a high yield, and such a separation requires combining two or more methods. For example, Sekiyukagaku Kogyo Handbook (Asakura Shoten, 1962), p. 178, FIGS. 7 and 6(B), illustrates a flow sheet for treating a $C_4$-fraction first in sulfuric acid-absorption apparatus to remove i-butene therefrom and then subjecting the residue to extractive distillation to obtain n-butenes. Further, Oil & Gas Journal, 55 (48), p. 87 states a process which comprises feeding the starting $C_4$-fraction to a starting material-preparing step comprising a sulfuric acid absorption unit and an extractive distillation unit to obtain a n-butene fraction freed from i-butene, i-butane and n-butane, feeding the said n-butene fraction to a butadiene synthesis step comprising a dehydrogenation unit and a product gas-treating unit to obtain a crude butadiene fraction, feeding the said crude butadiene fraction to a butadiene-purification step to obtain purified butadiene and at the same time to separate and recover the unreacted $C_4$-fraction composed mainly of n-butenes, and recycling the unreacted $C_4$-fraction thus recovered to the butadiene-synthesis step and/or the starting material preparation step. Further, UOP, 1978, Technology Conference H-23 describes a process for treating the starting $C_4$-fraction first in a sulfuric acid-absorption unit to remove i-butene therefrom and then feeding the residual fraction to a $C_4$-OLEX unit to remove butanes and to obtain n-butenes.

In all the processes mentioned above, the sulfuric acid absorption method is used for removing i-butene. As is apparent from Table 2, the use of etherification, vapor phase adsorption or dimerization in place of the sulfuric acid-absorption method can easily be predicted.

Figure 1:
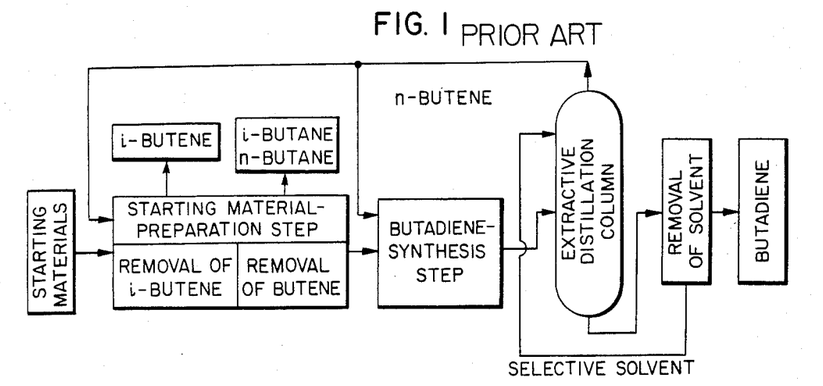
FIG. 1 is a flow sheet showing the prior art process for producing 1,3-butadiene.

In the accompanying drawings, FIG. 1 shows the whole process mentioned in Oil & Gas Journal, 55 (48), p. 87 which is a combination of the above-mentioned step of producing n-butenes (the starting material preparation step), the step of synthesizing butadiene by dehydrogenation or oxidative dehydrogenation and the step of purifying butadiene to obtain highly purified butadiene. That is, the starting $C_4$-fraction comprising $C_4$-paraffins and $C_4$-olefins is first sent to the starting material-preparation step where i-butene and $C_4$-paraffins are substantially completely removed therefrom. The n-butene fraction thus obtained is sent to the butadiene-synthesis step, and the resulting crude butadiene fraction is sent to the butadienepurification step. In the butadiene-purification step, the unreacted $C_4$ fraction is separated from butadiene and the major part of the unreacted $C_4$-fraction is returned to the butadiene-synthesis step. If separation of $C_4$-paraffins in the starting material-preparation step is insufficient, the $C_4$-paraffins are gradually accumulated in the system to seriously disturb the operation because $C_4$-paraffins are inert under the conditions of usual catalytic dehydrogenation or oxidative dehydrogenation of n-butene. For this reason, a part or the whole of the recycle stream from the butadiene-purification step is returned to the starting material-preparation step.

However, the production of n-butenes by the combination of the above-mentioned existing techniques becomes not only complicated in steps but also high in running cost. In addition, considering the competition of the butadiene produced from the n-butenes with the butadiene in the $C_4$-fraction formed as a by-product by the steam cracking of naphtha or the like, the former butadiene has a serious economical problem and is actually required to be improved.

The present inventors have conducted studies with the aim of solving the problems which the existing techniques have. As a result, they have reached an idea that a more rational process may be constructed by considering the starting material-preparation step for producing butadiene by dehydrogenation or oxidative dehydrogenation not independently but along with the butadiene-purification step, the two steps having a common problem of separating each of the components contained in the $C_4$-fraction. After an elaborate study for realizing the above idea, it has been found that utilizing the fact that n-butane which is difficult to separate together with i-butene from n-butenes in the starting material-purification step can easily be separated from n-butenes according to the extractive distillation method widely used in the butadiene-purification step, and it is allowable for butanes to be incorporated to a certain extent into the n-butenes to be fed to the butediene-synthesis step, the $C_4$-fraction freed substantially from i-butene (when lighter and/or heavier fractions than $C_4$ are contained, they have been removed by distillation or the like) can be fed to the middle stage of the extractive distillation column after or without passing through the butadiene-synthesis step, and a fraction composed mainly of $C_4$-paraffins can be distilled out of the column top while withdrawing a side vapor stream from a stage on the upper side of the stage of feeding the $C_4$-fraction containing butadiene from the butadiene-synthesis step and on the lower side of the stage of feeding a selective solvent that is near tne top of the column, whereby a fraction rich in n-butenes and containing decreased concentrations of $C_4$-paraffins and butadiene can be obtained as the side vapor and, on the other hand, a fraction consisting of the selective solvent and hydrocarbons composed mainly of butadiene and containing a small quantity of 2-butene, can be obtained from the bottom of the column.

SUMMARY OF THE INVENTION

According to this invention, there is provided a process for producing 1,3-butadiene which comprises feeding a fraction comprising as the main components $C_4$-paraffins and $C_4$-olefins and being substantially free from isobutene, 1,3-butadiene and $C_4$-acetylenes to a dehydrogenation or oxidative dehydrogenation step (step A) in which to convert the n-butenes to 1,3-butadiene, feeding the thus obtained hydrocarbon fraction containing 1,3-butadiene (fraction C) to an extractive distillation column (column B), distilling the fraction in an atmosphere of a selective solvent in column B to obtain a fraction comprising $C_4$-paraffins as the main hydrocarbon component from the top of the column while withdrawing a fraction comprising n-butenes as the main component as a side stream from a stage on the upper side of the fraction C-feeding stage and on the lower side of the selective solvent-feeding stage to recycle it to step A and while withdrawing a fraction comprising 1,3-butadiene as the main component and also containing the selective solvent and separating 1,3-butadiene therefrom (hereinafter, the above-mentioned process is referred to as "Process A") or alternatively which comprises feeding a fraction comprising as the main components $C_4$-paraffins and $C_4$-olefins and being substantialy free from isobutene (fraction D) to an extractive distillation column (column B); distilling fraction D in an atmosphere of a selective solvent in column B while obtaining a fraction comprising $C_4$-paraffins as the main hydrocarbon component from the column top and while withdrawing a fraction comprising n-butenes as the main component as a side stream from a stage on the upper side of the stage of feeding the $C_4$-hydrocarbon fraction containing 1,3-butadiene obtained from a dehydrogenation or oxidative dehydrogenation step (step A) and on the lower side of the selective solvent-feeding stage and feeding the side stream to step A in which to convert the n-butenes to 1,3-butadiene; feeding the resulting $C_4$-hydrocarbon fraction containing 1,3-butadiene to column B alone or in combination with fraction D; distilling the fraction in column B while withdrawing a fraction comprising 1,3-butadiene as the main hydrocarbon component and also containing the selective solvent from the bottom of the column, and separating the 1,3butadiene therefrom (hereinafter, referred to as "Process B").

BRIEF DESCRIPTION OF THE DRAWINGS

Hereunder, this invention is illustrated in more detail referring to the accompanying drawings, in which.

DETAILED DESCRIPTION OF THE INVENTION

Figure 2:
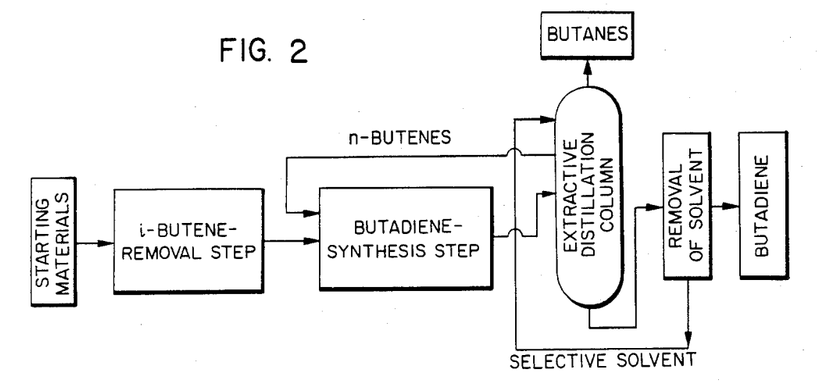
FIG. 2 and FIG. 3 are flow sheets showing the essential steps in Processes A and B, respectively, of this invention.
Figure 3:
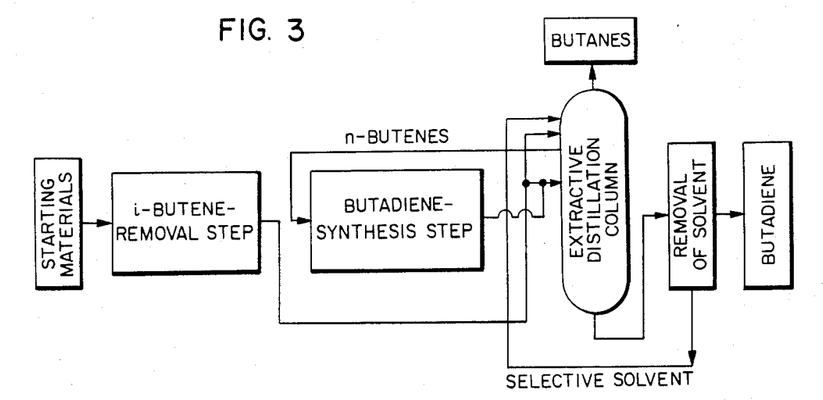

The characteristic feature of this invention consists in that the separation and removal of $C_4$-paraffins from the starting $C_4$-hydrocarbon fraction and/or the $C_4$-hydrocarbon fraction obtained from the butadiene-synthesis step and the recovery of $C_4$-olefins and the concentration and separation of butadiene are carried out in one extractive distillation column. That is, according to the process of this invention, they are carried out in one extractive distillation column as shown in FIGS. 2 and 3, and this is the fundamental difference from the prior process where separation of butanes, recovery of n-butenes and concentration and separation of butanes are carried out in separate extractive distillation columns as shown in FIG. 1. In FIG. 1, various extractive distillation processes as mentioned in, for example, Encyclopedia of Chemical Processing and Design, Vol. 5 (Marcel Dekker Inc. 1977), pp. 144–154 are applied to the extractive distillation step and subsequent steps, and an extractive distillation method is applied also to the removal of butanes in the starting material-preparation step as mentioned in Chemical Engineering, 39 (Feb. 1957), pp.146–148. On the other hand, in the present invention, the two extractive distillation steps are unified into one step as shown in FIG. 2 and FIG. 3. Accordingly, the process of this invention is greatly simplified, which brings about not only a reduction in installation cost but also a great reduction in operation cost.

Process A and Process B are identical with each other in that only isobutene is mainly separated in the starting material-preparation step without separating n-butenes, and the n-butenes and butanes present in the starting material are sent to the butadiene synthesis step or the extractive distillation column, and the n-butenes obtained are recycled to the butadiene synthesis step. However, Process B (FIG. 3) differs from Process A in that the $C_4$-hydrocarbon fraction freed from i-butene is directly sent to the extractive distillation column not via the butadiene-synthesis step, and the $C_4$-fraction containing butadiene from the butadiene-synthesis step is recycled to an appropriate stage of the extractive distillation column depending on the content of butadiene. In this invention, however, it is also possible to use Processes A and B in combination, i.e. to send part of the starting $C_4$-hydrocarbon to the butadiene-synthesis step according to flow shown in FIG. 2 and to feed the residual part to the extractive distillation column according to the flow shown in FIG. 3.

The starting $C_4$-hydrocarbon used in Process A is required to be substantially free from i-butene, and it is preferred that the other components be present in amounts within a certain range because the starting hydrocarbon is fed directly to the butadiene-synthesis step.

Although butanes are substantially inert in the butadiene-synthesis step and can be regarded as a mere diluent, too large a quantity of butanes not only reduces the efficiency of each unit in the butadiene-synthesis step but also brings about an increase in operation cost. Accordingly, the content of butanes is preferably 50% by weight or less, more preferably 30% by weight or less. Since butadiene reacts particlly to be consumed when fed to the butadiene synthesis step, it is not desirable that the $C_4$-hydrocarbon contains a large quantity of butadiene. In general, the content thereof is preferably 10% by weight or less, more preferably 5% by weight or less. When acetylenes are fed to the butadiene synthesis step, most thereof react to be consumed. However, too large a quantity of acetylenes adversely affect the stability of the reaction. Therefore, generally the quantity of acetylenes is preferably 5% by weight or less, more preferably 2% by weight or less.

On the other hand, the starting $C_4$-hydrocarbon used in Process B is not critical, except that it should be substantially free from i-butene. The starting materials containing butanes, butadiene and the like at high concentrations can also be treated by Process B.

In Process B of FIG. 3, the position of the feeding stage in the extractive distillation column may be varied depending upon the composition of the starting material, namely may be the same as the stage to which the fraction from the butadiene-synthesis step is fed, or may also be altered appropriately to realize a more efficient operation. For example, when the starting material is substantially free from butadiene, it is preferable from the viewpoint of the efficiency of extractive distillation to feed the starting material to a stage between the stage from which the side stream is withdrawn and the stage to which the selective solvent is fed. As the concentration of butadiene in the starting hydrocarbon increases, the feeding of the starting material to a stage in a lower position becomes more preferable.

In this invention, the fraction withdrawn from the bottom of the extractive distillation column, which consists of the selective solvent and the hydrocarbon comprising butadiene as the main component, can be purified to give high purity butadiene by the 1-stage and 2-stage extractive distillation processes described in, for example, Encyclopedia of Chemical Processing and Design, Vol. 5 (Marcel Dekker Inc., 1977), pp. 144–154.

Figure 4:
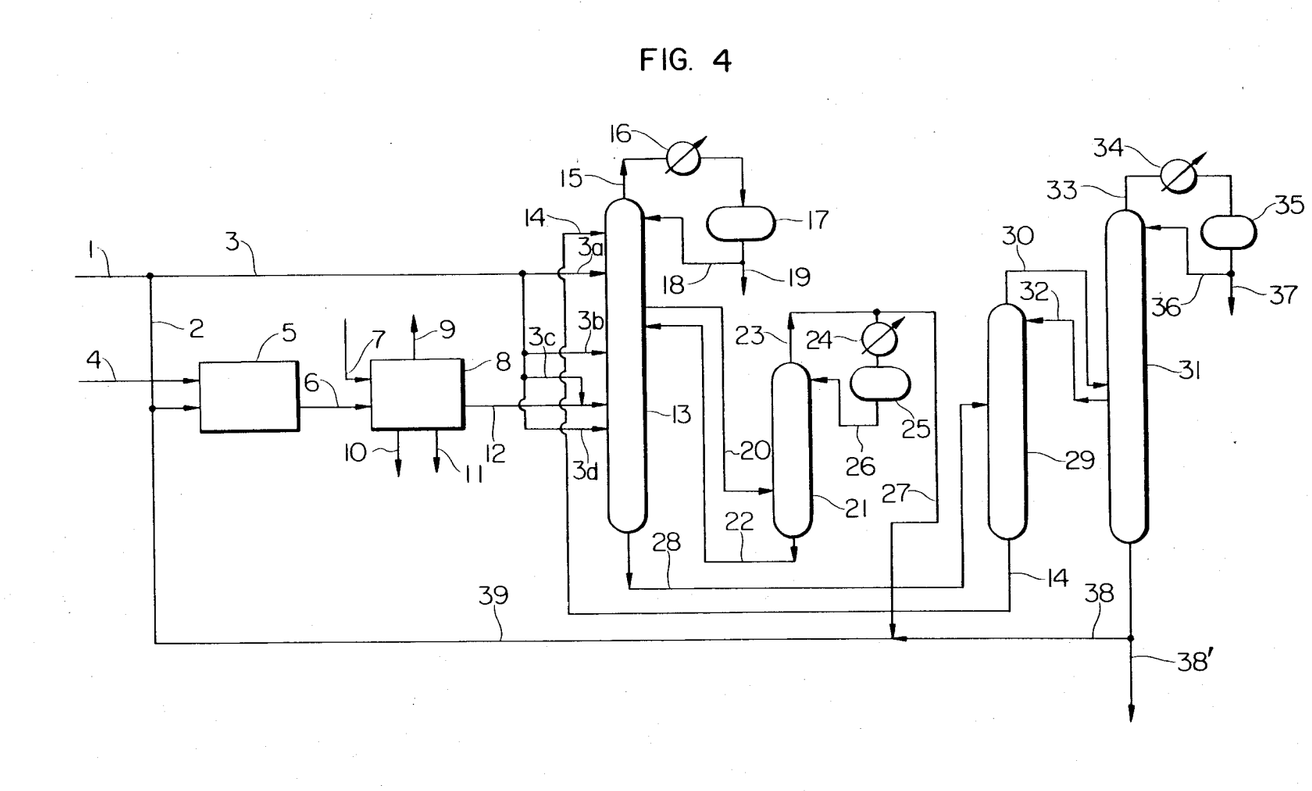
FIG. 4 is a flow sheet showing one embodiment of the production process of this invention.

FIG. 4 is a flow sheet showing an embodiment of the process of this invention for producing butadiene, in which a one-stage extractive distillation process is adopted for the purification of butadiene. In FIG. 4, the starting $C_4$-hydrocarbon fraction substantially free from i-butene is fed to the system through conduits 1 and 2 and/or a conduit 3. In Process A, the conduit 3 is not used and the starting material is fed to a butadiene-synthesizing unit 5 via the conduit 2. In Process B, the conduit 2 is not used and the starting material is fed to an extractive distillation column 13 via the conduit 3. In Process B, it is also possible to feed part of the starting material to a butadiene-synthesizing unit via the conduit 2 and feed the remainder to the extractive distillation column 13 via the conduit 3. However, Process A will be illustrated in the first place.

In the butadiene-synthesizing unit 5, dehydrogenation or oxidative dehydrogenation is carried out. Oxidative dehydrogenation is more preferable than the other because the oxidative dehydrogenation can enhance the reaction yield. Therefore, oxidative dehydrogenation is referred to below for explaining the operation in the unit 5. To the butadiene-synthesizing unit 5 is sent via a conduit 39, as the hydrocarbon fraction, a mixture of the stream from the conduit 2, the stream comprising n-butenes as the main component obtained via a conduit 27 as the overhead fraction of a butene-recovery column 21, and optionally the stream comprising as the main component 2-butene withdrawn from the bottom of a butadiene purification column 31 via a conduit 38. In addition, oxygen as an oxidant and an inert gas such as steam, nitrogen, carbon dioxide or the like as a diluent (usually, air or steam) are fed to the butadiene-synthesizing unit 5 via a conduit 4. As the said diluent, a non-condensable gas formed by recovering the condensable hydrocarbon fraction from the reaction product gas is also usable. The butadiene-synthesizing unit 5 using an oxidative dehydrogenation process and the gas-treating unit 8 are explained in, for example, Industrial and Engineering Chemistry, Vol. 62, No. 5, pp. 42–47 (1970), The Oil and Gas Journal, pp. 60–61 (Aug. 2, 1971), Hydrocarbon Processing, pp. 133–135 (June 1974), ibid. pp. 131–136 (Nov. 1978), etc.

In the butadiene-synthesizing unit 5, the formation of butadiene from n-butenes by oxidative dehydrogenation is an exothermic reaction of about 30 kcal/mole. By this reaction, a part of the n-butenes is further oxidized to CO or $CO_2$, and the heat generation by this oxidation cannot be neglected. Accordingly, the temperature control is quite important to allow the reaction to proceed smoothly. If the hydrocarbon to be fed to the reactor is diluted with much steam or the like to reduce the unit amount of heat generated of the reaction gas, an adiabatic reactor may also be used. In this case, however, the temperature of gas at the outlet of the reactor becomes much higher than the temperature of gas at the inlet, the use of a fixed bed type multitubular reactor or a fluidized bed reactor is preferable not only from the viewpoint of maintaining the performances of catalyst but also for enhancing the concentration of n-butenes in the gas fed to the reactor and for facilitating the treatment of the reaction product gas. As the catalyst for the oxidative dehydrogenation of n-butenes, known catalysis, such as ferrite type, P-Sn type, Sn-Sb type, Mo-Bi type and the like are used. Particularly, Mo-Bi type catalysts, and above all, Mo-Bi-Fe-Co-Sb$^{III}$-Sb$^V$ and Mo-Bi-Fe-Co-Ni-Sb$^{III}$-Sb$^V$ exhibit quite excellent performances. The oxidative dehydrogenation reaction is usually carried out at a temperature of 250°–600° C., at a pressure of 1–5 atms. and at a space velocity of 500–3,000 hr$^{-1}$, even though the optimum conditions may be varied depending upon the kind of the catalyst used.

The reaction product gas leaving the butadiene-synthesizing apparatus 5 is sent to, for example, a waste heat boiler for the purpose of recovering the heat, and then fed to gas-treating unit 8 via a conduit 6.

The gas-treating unit 8 is a unit for recovering hydrocarbons from a stream composed of the non-condensable gases, such as nitrogen, oxygen, CO, $CO_2$ and the like, steam, various hydrocarbons comprising as the main components $C_4$-fraction, including butadiene, a small quantity of oxygen-containing organic compounds; and other gases, which are obtained in the butadiene-synthesizing unit 5. As said apparatus, those expressed by the flow sheet mentioned in, for example, Industrial and Engineering Chemistry, Vol. 62, No. 5, pp. 42–47 (May 1970) or The Oil and Gas Journal, pp. 60–61 (Aug. 2, 1971) can be adopted. Via a conduit 7, water is introduced into the gas-treating unit 8 to wash away the small quantity of oxygen-containing organic compounds present in the reaction product gas. The washing water is combined with the steam fed from the conduit 4 and the condensate of the steam formed by the reaction, and discharged as waste water via a conduit 10 out of the system. On the other hand, the hydrocarbon fraction is freed from the absorbing oil and then optionally freed from the heavy oil formed in the butadiene-synthesizing unit 5 or the gas-treating unit 8 after discharging the heavy oil out of the system via a conduit 11, the remainder is fed to the middle stage of an extractive distillation column 13 via a conduit 12.

Via a conduit 14, a selective solvent is fed to the neighborhood of the top of an extractive distillation column 13. As the selective solvent, any solvent which is usable for the separation of butanes/butenes/butadiene may be used. Preferable examples of the solvent include acetone, acetonitrile, dimethylformamide, N-methylpyrrolidone, furfural and the like, mixtures of two or more of them, and their mixtures with water.

From the top of the extractive distillation column 13, a vapor stream is discharged via a conduit 15, which is condensed in a condenser 16 and sent to a reflux tank 17, where a part of the condensate is returned to the top of the column 13 as a reflux via conduit 18 and the residual part is discharged from the system via a conduit 19 as the overhead fraction. The overhead fraction comprises $C_4$-paraffins as the main hydrocarbon component, and the operation conditions are so controlled as to keep the loss of $C_4$-olefins at a low level. Since when some selective solvents are used a part thereof accompanies the overhead fraction, the overhead fraction is, if necessary, washed with water or the like to recover the solvent and simultaneously purify the hydrocarbon.

Via a conduit 20, a vapor stream is withdrawn as a side stream from the extractive distillation column 13 at a stage between the stage to which the conduit 12 from the gas-treating unit 8 is connected and the selective solvent-feeding stage, and the side stream is fed to the bottom of a butene-recovery column 21. On the other hand, a liquid stream is withdrawn from the bottom of the butene-recovery column 21 via a conduit 22, and fed to the extractive distillation column 13 at a stage close to, preferably same as, the stage from which the above-mentioned side stream is withdrawn as a vapor stream.

On the other hand, from the bottom of the extractive distillation column 13, a mixture consisting of the selective solvent and a hydrocarbon component comprising butadiene as the main component is withdrawn via a conduit 28, and fed to the middle stage of a stripping column 29. Although the content of $C_4$-olefins in the hydrocarbon component of this bottom fraction can be decreased to substantially zero % by appropriately selecting the operation conditons, a small quantity of 2-butene is usually present in the bottom fraction. In addition, when $C_4$-acetylenes are present in the starting material fed from a conduit 12, the $C_4$-acetylenes are wholly contained in the bottom fraction.

The butene-recovery column 21 is, for example, a tray column having 5–20 trays, for separating the selective solvent from the hydrocarbon component. A vapor stream is withdrawn from the top of the column via a conduit 23. A part of the vapor is condensed in a condenser 24, and the remainder is sent to a reflux tank 25 and the whole thereof is returned as the reflux to the top of the butene-recovery column 21. The remainder is not condensed and fed, as the overhead fraction, to the butadiene-synthesizing unit 5 via a conduit 27 and then via a conduit 39. When some selective solvents are used, the overhead fraction contains a part of the solvent entrained. In such a case, the solvent is removed from the stream by an operation such a water-washing or the like and then the solvent-freed overhead fraction is fed to the butadiene-synthesizing unit 5.

The hydrocarbons contained in the overhead fraction of the butene-recovery column 21 obtained via a conduit 27 comprise n-butenes as the main component and also contain a small quantity of $C_4$-paraffins. However, the conditions are set so that the butadiene concentration is kept as low as possible. The quantity of $C_4$-paraffins in the stream obtained via a conduit 27 is controlled to 50% or less, preferably 30% or less, based on the quantity of $C_4$-paraffins in the stream fed via the conduit 12. If the quantity exceeds 50%, the concentration of $C_4$-paraffins in the total hydrocarbons fed to the butadiene synthesis step can become too high in some cases.

On the other hand, the quantity of butadiene in the stream withdrawn via a conduit 27 is controlled to 10% or less, preferably 5% or less, based on the concentration of butadiene in the stream fed via the conduits 3 and 12. If the quantity exceeds 10%, the loss of butadiene caused by reaction in the butadiene-synthesis step increases and, in addition, the amount recycled increases, resulting in an elevation of the operation cost. No reboiler is usually necessary at the bottom of the butene-recovery column 21, because the heat for the operation of this column is totally supplied by the vapor stream sent from the conduit 20.

The stripping column 29 may be an independent column provided with a condenser and a reflux tank at its top similarly to the column 13 or 21. However, it is more preferable from the viewpoint of energy saving to thermally connect this column to the butadiene-purification column 31 as mentioned in, for example, Japanese patent application Kokai (Laid-Open) No. 128,724/81. In this case, the vapor stream withdrawn from the top of stripping column 29 via a conduit 30 is fed directly to the middle stage of the butadiene purification column 31. On the other hand, a liquid stream is withdrawn from the butadiene-purification column 31 at a stage close to, preferably the same as, the feeding stage of the conduit 30, as a side stream, and fed to the top of the stripping column 29 as a reflux to the stripping column. From the bottom of the stripping column, a stream composed substantially of the selective solvent is withdrawn, which is cooled to an appropriate temperature while passing a heat exchanger (not shown) and a cooler for the sake of recovering heat, and then recycled to the extractive distillation column 13 via the conduit 14. Since in the selective solvent the heavy fraction is gradually accumulated during recycling and the accumulated heavy fraction causes a trouble on the continuous operation, a part of the circulated stream is preferably withdrawn, purified in a solvent-purification step (not shown) and then returned to the circulating system.

From the top of the butadiene-purification column 31, a vapor stream is withdrawn via the conduit 33. This is condensed in the condenser 34 and the condensate is sent to the reflux tank 35, where a part of the stream is returned to the top of the butadiene-purification column 31 via a conduit 36 as a reflux and the remainder is discharged from the system via a conduit 37 as the overhead fraction. This fraction is composed substantially of butadiene, and therefore, can usually be used as product butadiene as it is. When this fraction contains a large quantity of acetylenes, it is deacetylated by extractive distillation or the like, and thereafter used as product butadiene. On the other hand, from the bottom of the butadiene-purification column 31, a fraction comprising 2butene as the main component and also containing a small quantity of butadiene is withdrawn via the conduit 38. Though this is usually recycled to the butadiene-synthesizing unit 5, it may also be discharged from the system via a conduit 38' when the concentration of 2-butene is low and the concentration of heavy component is high in this fraction.

The columns 13, 29 and 31 are provided with a reboiler (not shown in FIG. 4) for the purpose of supplying the heat necessary for their operation. The pipeline system involves valves and the like, too, though they are not shown in FIG. 4.

Next, an example of Process B will be illustrated similarly referring to FIG. 4. The starting $C_4$-hydrocarbon fraction substantially free from i-butene is fed to the middle stage of the extractive distillation column 13 via the conduit 1 and then via the conduit 3. Although the starting hydrocarbon-feeding stage may be the same as the stage to which the gas sent from the gas-treating unit 8 via the conduit 12 is fed (conduit 3c), the starting hydrocarbon-feeding stage is preferably altered from 3a to 3b, 3c or 3d, depending on the composition of the stream in the conduit 3. That is, when the starting $C_4$-hydrocarbon fed via the conduit 3 is substantially free from butadiene, it is preferably fed via the conduit 3a to a stage between the stage from which the side stream is withdrawn via the conduit 20 and the stage to which the selective solvent is fed. As the concentration of butadiene in the starting $C_4$-hydrocarbon increases, the starting hydrocarbon-feeding line is preferably converted to a lower stage of the extractive distillation column, for example, the conduit 3b, the conduit 3c and further the conduit 3d. The other parts than explained above of Process B are just the same as those of Process A, except that the conduit 2 is not used and that the starting $C_4$-hydrocarbon to be fed to the butadiene-synthesizing unit 5 is the stream from the butene-recovery step through the conduit 39.

In the case of combination of Process A and Process B where a part of the starting $C_4$-hydrocarbon substantial free from i-butene is fed to the butadiene-synthesizing unit 5 via the conduit 2 and the remainder is fed to the extractive distillation column 13 via the conduit 3, the illustration of the process is just the same as the illustrations of process A and process B, except that the starting $C_4$-hydrocarbon is fed from both conduits 2 and 3.

This invention will be explained in more detail below referring to Examples.

EXAMPLE 1

Process A was performed according to the flow sheet of FIG. 4. Thus, 9,586 kg/hr of a $C_4$-hydrocarbon fraction having the composition shown in Table 3 was fed to the butadiene-synthesizing unit 5 via the conduits 1 and 2 (without using the conduit 3) together with 1,533 kg/hr of a recycle stream fed via the conduit 39. At the same time, 24,807 kg/hr of air and 4,091 kg/hr of steam were fed to the butadiene-synthesizing unit 5 via the conduit 4. The oxidative dehydrogenation reactor constituting the butadiene-synthesizing unit 5 was a multitubular reactor composed of tubes having an inner diameter of 28 mm, and the inner spaces of the tubes were filled with spherical catalysts having a particle diameter of about 5 mm prepared by supporting a composite oxide of Mo-Bi-Fe-Co-Sb(III)-Sb(V) on $\alpha$-alumina carrier having a particle diameter of 4 mm as mentioned in Japanese Patent Publication No. 41,648/78. Through the outer spaces of the tubes, a molten salt was circulated (inlet temperature 340° C.) to control the reaction temperature. The reaction was carried out at a pressure (at the inlet of the reactor) of 1.7 atms. and a temperature of 340° C. As a result, 85% of the n-butenes fed to the reactor was reacted, 88% of which was converted to butadiene. The reaction product gas leaving the butadiene-synthesizing unit 5 was fed to the gas-treating unit 8 via the conduct 6.

The gas-treating unit 8 comprised a step of rapidly cooling the reaction product gas, a step of compressing the gas, a step of removing the oxygen-containing compounds formed by the reaction by washing the gas with water, and a step of recovering the hydrocarbon fraction from a large quantity of non-condensable gas by a gas absorption process. To the system was fed, via the conduit 7, 32,242 kg/hr of washing water for removing the oxygen-containing compounds, while 39,827 kg/hr of waste water containing the oxygen-containing compounds, 148 kg/hr of a heavy component and 22,628 kg/hr of a stream composed mainly of non-condensable gas were discharged from the system via the conduits 10, 11 and 9, respectively. Thus, 9,456 kg/hr of a hydrocarbon fraction having the composition shown in Table 3 was obtained from the conduit 12, and this stream was subsequently fed to the middle stage of the extractive distillation column 13.

To the neighborhood of the top of the extractive distillation column 13, 51,235 kg/hr of a solvent composed of 92% by weight of acetonitrile and 8% by weight of water was fed via the conduit 14 at a temperature of 53° C. From a stage between the starting material-feeding stage and the solvent-feeding stage of the extractive distillation column 13, 5,551 kg/hr of a side stream was withdrawn via the conduit 20 as a vapor stream, and fed to the bottom of the butene-recovery column 21. On the other hand, 4,056 kg/hr of the bottom fraction of the butene-recovery column 21 was fed to the same stage as the side stream-withdrawing stage via the conduit 22.

The extractive distillation column 13 was operated at a column top pressure of 4.5 atms., a column top temperature of 47° C. and a column bottom temperature of 109° C. Thus, 1,633 kg/hr of an overhead fraction having the composition shown in Table 3, which was composed mainly of n-butane, was obtained via the conduit 19, and 57,674 kg/hr of a stream composed of the solvent and a hydrocarbon component (composed mainly of butadiene) was withdrawn from the bottom via the conduit 28, which was then fed to the middle stage of the stripping column 29. In a reflux tank 17, though not shown in FIG. 4 a small quantity of a water-rich phase separated. Therefore, this was subjected to layer-separation, and withdrawn out of the system at a flow rate of 89 kg/hr. This stream was an aqueous solution containing 7% by weight of acetonitrile. The stream withdrawn from the conduit 19 contained a considerable quantity of acetonitrile, and hence, after removing the acetonitrile therefrom by washing with water in a washing column (not shown), was discharged out of the system.

The butene-recovery column 21 was operated at a column top pressure of 4.5 atms., a column top temperature of 48° C. and a column bottom temperature of 59° C. Thus, 1,466 kg/hr of an overhead fraction composed mainly of n-butenes and n-butane and having the composition shown in Table 3 was withdrawn from the conduit 27 as a vapor stream. This stream contained a considerable quantity of acetonitrile, and hence, after removing the acetonitrile therefrom by washing with water in a washing column (not shown), was recycled to the butadiene-synthsizing unit 5. In a reflux tank 25, though not shown in FIG. 4, a small quantity of a water-rich phase separated. Therefore, this was subjected to layer separation and then discharged out of the system at a flow rate of 29 kg/hr. This stream was an aqueous solution containing 4% by weight of acetonitrile.

The stripping column 29 was operated at a column top pressure of 5.2 atms., a column top temperature of 43° C. and a column bottom temperature of 134° C. From the column top, 23,223 kg/hr of a vapor stream was withdrawn via the conduit 30 and fed to the middle stage of the butadiene-purification column 31. On the other hand, 16,525 kg/hr of a liquid stream was withdrawn from the butadiene-purification column 31 at the same as the stage to which the conduit 30 was connected, and fed to the top of the stripping column 29 via the conduit 32 as a reflux. Thus, from the bottom of the stripping column 29, 50,978 kg/hr of a solvent substantially free from hydrocarbons was withdrawn, and recycled to the extractive distillation column 13 via the conduit 14. Since heavy oils and the like were gradually accumulated in the solvent stream circulated during recycling and this accumulation caused a trouble on the smooth continuous operation, 510 kg/hr (corresponding to 1% of the circulating stream) of the solvent stream circulated was withdrawn, treated in solvent-purification apparatus (not shown) and returned to the solvent stream circulated. The aqueous acetonitrile solution recovered by washing the streams of the conduits 19 and 27 with water, and the aqueous phases separated from the hydrocarbon phases in the reflux tanks 17 and 25 were combined and treated to concentrate and recover the acetonitrile. The recovered acetonitrile was returned to the solvent-circulating system.

The butadiene-purification column 31 was operated at a column top pressure of 4.4 atms., a column top temperature of 41° C. and a column bottom temperature of 54° C. Thus, as the overhead fraction and the bottom fraction, the fractions having the compositions shown in Table 3 were obtained at a rate of 6,525 kg/hr and 83 kg/hr, respectively, via the conduits 37 and 38. Generally speaking, the former stream may further be purified, if necessary. However, when the oxidative dehydrogenation catalyst system shown in this Example was used, the formation of $C_4$-acetylenes was so slight that no further purification was required, and butadiene of high purity was obtained as a product. On the other hand, the latter stream was recycled to the butadiene-synthesizing unit 5.

TABLE 3

| | (Composition: % by weight) | | | | | |
|---|---|---|---|---|---|---|
| Conduit No. | 1, 2 | 12 | 19 | 27 | 37 | 38 |
| $C_3$ or lower | | | | | | |
| i-Butane | | | | | | |
| n-Butane | 16.9 | 16.6 | 95.7 | 13.6 | | |
| i-Butene | 0.5 | | | | | |
| 1-Butene | 0.1 | | | | | |
| trans-2-Butene | 53.6 | 12.1 | 2.8 | 73.1 | 0.3 | 9.6 |
| cis-2-Butene | 27.7 | 2.1 | | 9.5 | 0.1 | 67.2 |
| 1,3-Butadiene | | 69.1 | | 1.8 | 99.6 | 7.8 |
| $C_4$—Acetylenes | | | | | (40 ppm) | 0.1 |
| Other $C_4$ | | | | | | |
| $C_5$ or higher | 1.2 | 0.1 | | | | 15.3 |
| Total Hydrocarbon | 100.0 | 100.0 | 98.5 | 98.0 | 100.0 | 100.0 |
| Acetonitrile | | | 1.4 | 1.3 | | |
| Water | | | 0.1 | 0.7 | | |
| Total solvent | | | 1.5 | 2.0 | | |
| Total | 100.0 | 100.0 | 100.0 | 100.0 | 100.0 | 100.0 |

EXAMPLE 2

Process B was performed according to the flow sheet of FIG. 4. Thus, 18,566 kg/hr of a $C_4$-hydrocarbon fraction having the composition shown in Table 4 was fed to the middle stage of the extractive distillation column 13 via the conduits 1 and 3 (without using the conduit 2) and finally via the conduit 3a.

To the neighborhood of the top of the extractive distillation column 13, 108,271 kg/hr of a solvent composed of 92% by weight of acetonitrile and 8% by weight of water was fed via the conduit 14 at a temperature of 53° C. Via the conduit 20, 35,615 kg/hr of a side stream was withdrawn, as a vapor stream, from a stage between the solvent-feeding stage and the stage of the extractive distillation column 13 to which the conduit 12 from the gas-treating unit 8 (mentioned later) was connected, and fed to the bottom of the butene-recovery column 21. On the other hand, 26,024 kg/hr of the bottom fraction of the butene-recovery column 21 was fed to the same stage as the side stream-withdrawing stage via the conduit 22.

The extractive distillation column 13 was operated at a column top pressure of 4.5 atms., a column top temperature of 47° C. and a column bottom temperature of 111° C. Thus, as the overhead fraction, 11,205 kg/hr of a fraction composed mainly of the $C_4$-paraffins, which had the composition shown in Table 4, was obtained via the conduit 19. From the bottom, 113,627 kg/hr of a stream consisting of the solvent and a hydrocarbon component composed mainly of butadiene was withdrawn via the conduit 28 and fed to the middle stage of the stripping column 29. In a reflux tank 17, though not shown in FIG. 4, a small quantity of water-rich phase separated. Therefore, this was subjected to layer-separation, and then withdrawn out of the system at a flow rate of 622 kg/hr. This stream was an aqueous solution containing 7% by weight of acetonitrile. Since the stream withdrawn via the conduit 19 contained a considerable quantity of acetonitrile, this was subjected to water-washing to remove the acetonitrile in a washing column (not shown) and then dicharged out of the system.

The butene-recovery column 21 was operated at a column top pressure of 4.5 atms., a column top temperature of 48° C. and a column bottom temperature of 59° C. Thus, as the overhead fraction, 9,406 kg/hr of a fraction composed mainly of n-butenes and n-butane, which had the composition shown in Table 4, was withdrawn as a vapor stream via the conduit 27. Since this stream contained a considerable quantity of acetonitrile, this was subjected to water-washing to remove the acetonitrile in a washing column (not shown) and then fed to butadiene-synthesizing unit 5 via the conduit 39. In a reflux tank 25, though not shown in FIG. 4, a small quantity of water-rich phase separated. This was, therefore, subjected to layer-separation, and then discharged out of the system at a flow rate of 185 kg/hr. This stream was an aqueous solution containing 4% by weight of acetonitrile.

The stripping column 29 was operated at a column top pressure of 5.2 atms., a column top temperature of 47° C. and a column bottom temperature of 134° C. Thus, from the top, 22,820 kg/hr of a vapor stream was withdrawn via the conduit 30 and fed to the middle stage of the butadiene-purification column 31. On the other hand, from the stage of the butadiene-purification column 31 to which the conduit 30 was connected, 16,238 kg/hr of a liquid stream was withdrawn via the conduit 32, and fed to the top of the stripping column 29 as a reflux. Thus, 107,045 kg/hr of a solvent substantially free from hydrocarbon was withdrawn from the bottom of the stripping column 29 and recycled to the extractive distillation column 13 via the conduit 14. Since the heavy oil component and the like were gradually accumulated in this solvent stream circulated and this accumulation caused a trouble on the smooth continuous operation, 1,070 kg/hr (corresponding to 1% of the stream circulated) of the stream circulated was withdrawn from the system, treated in solvent-purification apparatus not shown in FIG. 4, and then returned to the solvent stream circulated. The aqueous acetonitrile solution recovered by washing the streams of the conduit 19 and the conduit 27 with water and the aqueous phases separated from the hydrocarbon phase in the reflux tanks 17 and 25 were combined and treated to concentrate and recover the acetonitrile. The recovered solvent was returned to the solvent-circulating system.

The butadiene-purification column 31 was operated at a column top pressure of 4.4 atms., a column top temperature of 41° C. and a column bottom temperature of 54° C. Thus, as the overhead fraction and the bottom fraction, fractions having the compositions shown in Table 4 were obtained at a rate of 6,413 kg/hr and 82 kg/hr, respectively, via the conduits 37 and 38. The latter stream was recycled to the butadiene-synthesizing unit 5 through the conduit 39.

To the butadiene-synthesizing unit 5 was fed 9,382 kg/hr of a hydrocarbon fraction via the conduit 39. On the other hand, 23,575 kg/hr of air and 3,887 kg/hr of steam were fed thereto via the conduit 4. The shape of the oxidative dehydrogenation reactor and the catalyst used were the same as in Example 1, and the reaction temperature was controlled by circulating a molten salt of 330° C. through the shell side of the reactor. The reaction was carried out at a pressure (at the inlet of the reactor) of 1.7 atms. at a temperature of 325° C. As a result, 85% of the n-butenes fed to the reactor were reacted, 90% of which was converted to butadiene.

The reaction product gas leaving the butadiene-synthesizing unit 5 was passed through the conduit 6 and then fed to the gas-treating unit 8.

The gas-treating unit 8 was operated under the same conditions as in Example 1, except that the streams in the conduits were so different as shown in Table 5. Thus, a $C_4$-fraction containing butadiene, which had the composition shown in Table 4, was obtained from the conduit 12, and fed to the middle stage of the extractive distillation column 13.

TABLE 4

| Conduit No. | (Composition: % by weight) | | | | | |
| --- | --- | --- | --- | --- | --- | --- |
| | 1, 3 | 12 | 19 | 27 | 37 | 38 |
| $C_3$ or lower | 3.9 | | 6.4 | | | |
| i-Butane | 41.7 | 0.3 | 69.0 | 0.2 | | |
| n-Butane | 13.6 | 6.3 | 22.4 | 5.7 | | |
| i-Butene | 0.1 | | | 0.2 | | |
| 1-Butene | 14.0 | 0.3 | 0.9 | 26.8 | | |
| trans-2-Butene | 15.5 | 11.3 | | 40.2 | 0.3 | 9.6 |
| cis-2-Butene | 11.0 | 3.7 | | 24.2 | 0.1 | 67.2 |
| 1,3-Butadiene | 0.2 | 78.0 | | 0.7 | 99.6 | 7.8 |
| $C_4$—Acetylenes | | | | | (40 ppm) | 0.1 |
| Other $C_4$ | | | | | | |
| $C_5$ or higher | | 0.1 | | | | 15.3 |
| Total hydrocarbon | 100.0 | 100.0 | 98.7 | 98.0 | 100.0 | 100.0 |
| Acetonitrile | | | 1.3 | 1.3 | | |
| Water | | | | 0.7 | | |
| Total solvent | | | 1.3 | 2.0 | | |
| Total | 100.0 | 100.0 | 100.0 | 100.0 | 100.0 | 100.0 |

TABLE 5

| Conduit 7 | 30,653 kg/hr |
| --- | --- |
| Conduit 9 | 21,422 kg/hr |
| Conduit 10 | 37,741 kg/hr |
| Conduit 11 | 126 kg/hr |
| Conduit 12 | 8,208 kg/hr |

In this Example, the stream obtained from the conduit 37 was composed substantially of butadiene, and if necessary, therefore, further purified. When the oxidative dehydrogenation catalyst shown in this Example was used, the formation of $C_4$-acetylenes was so slight that no further purification was required and butadiene of high purity was obtained as a product.

EXAMPLE 3

The procedure of Example 2 was repeated, except that a $C_4$-hydrocarbon containing about 55% by weight of butadiene and having the composition shown in Table 7 was used as the starting material and the feeding stage of the extractive distillation column 13 was altered from the conduit 3a to the conduit 3c. Table 6 indicates the flow rates in the main conduits, and Table 7 shows the compositions of the streams.

The starting $C_4$-hydrocarbon fraction used in this Example was prepared by thermally cracking naphtha to obtain a $C_4$-fraction, removing isobutylene therefrom and then removing acetylenes therefrom by a selective hydrogenation. The stream from the conduit 37 was able to be used as product butadiene without further purification.

TABLE 6

| Conduit No. | Flow rate (kg/hr) | Conduit No. | Flow rate (kg/hr) |
|---|---|---|---|
| 1, 3 | 7,609 | 32 | 16,758 |
| 14 | 49,435 | 37 | 6,413 |
| 19 | 801 | 38 | 290 |
| 20 | 11,113 | 4 Air | 8,017 |
| 22 | 8,120 | Steam | 1,324 |
| 27 | 2,935 | 7 | 10,441 |
| 28 | 55,965 | 9 | 7,290 |
| 30 | 23,548 | 10 | 12,886 |
| | | 11 | 42 |
| | | 12 | 2,759 |

TABLE 7

(Composition: % by weight)

| Conduit No. | 1, 3 | 12 | 19 | 27 | 37 | 38 |
|---|---|---|---|---|---|---|
| $C_3$ or lower | 0.6 | | 5.0 | 0.3 | | |
| i-Butane | 1.4 | 1.1 | 12.7 | 1.1 | | |
| n-Butane | 7.2 | 8.9 | 67.5 | 8.6 | | |
| i-Butene | 0.1 | | | 0.3 | | |
| 1-Butene | 23.1 | 0.6 | 13.5 | 56.5 | 0.1 | |
| trans-2-Butene | 7.2 | 6.2 | | 21.7 | 0.5 | 18.1 |
| cis-2-Butene | 4.6 | 1.8 | | 7.3 | 0.1 | 62.1 |
| 1,3-Butadiene | 55.5 | 81.3 | | 2.2 | 99.3 | 11.0 |
| $C_4$—Acetylenes | | | | | (40 ppm) | 0.1 |
| Other $C_4$ | 0.2 | | | | | 4.7 |
| $C_5$ or higher | 0.1 | 0.1 | | | | 4.0 |
| Total hydrocarbon | 100.0 | 100.0 | 98.7 | 98.0 | 100.0 | 100.0 |
| Acetonitrile | | | 1.3 | 1.3 | | |
| Water | | | | 0.7 | | |
| Total solvent | | | 1.3 | 2.0 | | |
| Total | 100.0 | 100.0 | 100.0 | 100.0 | 100.0 | 100.0 |

As mentioned above, according to the process of this invention, only i-butene is removed from the starting $C_4$-hydrocarbon material, and paraffins are left as they are in the starting material. The i-butene-freed starting material is subjected to extractive distillation before or after the butadiene-synthesis step. In the extractive distillation step, recovery of n-butenes, separation and removal of paraffins and concentration of butadiene are carried out simultaneously. Thus, unlike the conventional process, the process of this invention necessitates no step for removing paraffins before the butadiene synthesis. Therefore, simplification of process and reduction of the installation and operation costs can be achieved. Further, in sending the i-butene-freed starting material to the extractive distillation step directly, no restriction is placed on the starting material, except that it should be substantially free from i-butene. Accordingly, the starting materials containing butanes, butadiene and the like at a high concentration are also usable, and this fact enhances the general applicability of the process.

What is claimed is:

1. A process for producing 1,3-butadiene which comprises feeding a fraction comprising as the main components $C_4$-paraffins and $C_4$-olefins but substantially free from isobutene, 1,3-butadiene and $C_4$-acetylenes to a dehydrogenation or oxidative dehydrogenation step (step A); converting the n-butenes contained therein to 1,3-butadiene in step A; feeding the resulting hydrocarbon fraction containing 1,3-butadiene (fraction C) to an extractive distillation column (column B); and distilling said fraction in the presence of a selective solvent in column B while withdrawing a fraction comprising as the main component $C_4$-paraffins from the top of column B, withdrawing as a side stream a fraction comprising n-butenes as the main component from a stage on the upper side of the fraction C-feeding stage and on the lower side of the selective solvent-feeding stage and recycling the side stream to step A, and while withdrawing a fraction comprising 1,3-butadiene as the main hydrocarbon component and also containing the selective solvent component from the bottom of column B and separating 1,3-butadiene therefrom.

2. A process according to claim 1, wherein the fraction comprising as the main component n-butenes withdrawn as a side stream is fed to the bottom of another distillation column (column E) without being recycled to step A, thereby obtaining a hydrocarbon fraction containing further concentrated n-butenes as an overhead fraction of column E; and the hydrocarbon fraction is recycled to step A, and at the same time, the bottom fraction of column E is returned to a stage of column B in the vicinity of the side stream-withdrawing stage.

3. A process for producing 1,3-butadiene, which comprises feeding a fraction comprising as the main components $C_4$-paraffins and $C_4$-olefins but substantially free from isobutene (fraction D) to an extractive distillation column (column B); distilling the fraction in the presence of a selective solvent in column B while withdrawing a fraction comprising $C_4$-paraffins as the main hydrocarbon component from the top of column B, and while withdrawing as a side stream a fraction comprising n-butenes as the main component from a stage on the lower side of the selective solvent-feeding stage and on the upper side of the stage to which the $C_4$-hydrocarbon fraction containing 1,3-butadiene obtained from the dehydrogenation or oxdative dehydrogenation step (step A) is fed and feeding the side stream to step A to convert the n-butenes to 1,3-butadiene; feeding the thus obtained 1,3-butadiene-containing $C_4$-hydrocarbon fraction, alone or in combination with fraction D, to column B; and distilling the fraction in column B while withdrawing a fraction comprising 1,3-butadiene as the main hydrocarbon component and also containing the selective solvent from the bottom of column B and separating 1,3-butadiene from said fraction.

4. A process according to claim 3, wherein the fraction comprising n-butenes as the main component withdrawn as a side stream is fed to the bottom of another distillation column (column E) without being recycled to step A, thereby obtaining a hydrocarbon fraction containing further concentrated n-butenes as the overhead fraction of column E and recycling it to step A, and at the same time, returning the bottom fraction of column E to a stage of column B in the vicinity of the side streamwithdrawing stage.

* * * * *